(12) United States Patent
Stansbury

(10) Patent No.: US 8,882,075 B2
(45) Date of Patent: Nov. 11, 2014

(54) FURNACE MOUNT

(76) Inventor: Mark A Stansbury, Indianapolis, IN (US)

( * ) Notice: Subject to any disclaimer, the term of this patent is extended or adjusted under 35 U.S.C. 154(b) by 0 days.

(21) Appl. No.: 13/610,533

(22) Filed: Sep. 11, 2012

(65) Prior Publication Data

US 2013/0181107 A1 Jul. 18, 2013

Related U.S. Application Data

(63) Continuation of application No. 10/669,829, filed on Sep. 24, 2003, now Pat. No. 8,262,054, which is a continuation of application No. 09/941,524, filed on Aug. 29, 2001, now abandoned.

(60) Provisional application No. 60/264,955, filed on Jan. 30, 2001.

(51) Int. Cl.
| | |
|---|---|
| F16M 1/00 | (2006.01) |
| F16M 11/22 | (2006.01) |
| F24H 9/06 | (2006.01) |
| C07D 211/26 | (2006.01) |
| C07C 335/26 | (2006.01) |
| C07D 211/28 | (2006.01) |
| C07D 207/404 | (2006.01) |
| F16M 11/00 | (2006.01) |

(52) U.S. Cl.
CPC ................. *F16M 11/22* (2013.01); *F24H 9/06* (2013.01); *C07D 211/26* (2013.01); *C07C 2101/14* (2013.01); *C07C 335/26* (2013.01); *C07D 211/28* (2013.01); *F16M 2200/08* (2013.01); *C07D 207/404* (2013.01); *F16M 11/00* (2013.01)
USPC ......................... 248/677; 248/634; 248/188.1

(58) Field of Classification Search
CPC ...... A47B 2091/063; A47B 91/12; F16F 1/37
USPC ......... 248/678, 677, 634, 633, 609, 615, 638, 248/673, 188.1, 188.5, 188.3, 346.5, 346.11
See application file for complete search history.

(56) References Cited

U.S. PATENT DOCUMENTS

| | | | | |
|---|---|---|---|---|
| 1,179,811 | A * | 4/1916 | Diss | 16/42 R |
| 1,647,828 | A * | 11/1927 | Griswold | 126/67 |
| 1,880,153 | A * | 9/1932 | Rosenzweig | 181/207 |
| 1,887,283 | A * | 11/1932 | Brabson | 248/346.11 |
| 2,941,329 | A * | 6/1960 | Apparius | 248/188.2 |
| 3,311,331 | A * | 3/1967 | Steimen | 248/633 |
| 3,326,508 | A * | 6/1967 | Born | 248/346.11 |
| 3,583,215 | A * | 6/1971 | Franz | 73/844 |
| 4,721,275 | A * | 1/1988 | Benton et al. | 248/188.4 |
| 4,842,095 | A * | 6/1989 | Rozek | 181/207 |
| 4,856,438 | A * | 8/1989 | Peugh | 110/233 |
| D465,022 | S * | 10/2002 | Stansbury | D23/386 |
| 8,262,054 | B2 * | 9/2012 | Stansbury | 248/677 |

\* cited by examiner

*Primary Examiner* — Anita M King
(74) *Attorney, Agent, or Firm* — Krieg DeVault LLP

(57) ABSTRACT

A furnace mounting system to elevate the furnace above the floor. In one form the furnace mounting system includes a furnace mounting block including a vibration dampening feature to prevent the transmission of noise and vibration from the furnace to the mounting block. The furnace mounting block includes a locating feature and is adhered to the bottom surface of the furnace.

14 Claims, 4 Drawing Sheets

FURNACE MOUNT

The present application is a continuation of U.S. patent application Ser. No. 10/669,829 filed on Sep. 24, 2003 and now U.S. Pat. No. 8,262,054. application Ser. No. 10/669,829 is a continuation of U.S. patent application Ser. No. 09/941,524 filed on Aug. 29, 2001 and now abandoned. Application Ser. No. 09/941,524 claims the benefit of U.S. Provisional Patent Application No. 60/264,955 filed Jan. 30, 2001. Each of the above applications are incorporated herein by reference.

BACKGROUND OF THE INVENTION

The present invention relates generally to a method and apparatus for supporting a furnace. More particularly, the present invention has one form wherein a plurality of furnace mounting blocks are adhered to the bottom of the furnace and maintain the furnace in a position off of the floor.

It is well known that furnaces are conventionally utilized to deliver heated air through a furnace duct system to heat registers located throughout the house. The furnaces are generally raised off of the floor to avoid being exposed to moisture and the associated rusting of the furnace cabinet. In one prior technique of raising the furnace off the floor, the installation technicians have utilized masonry blocks which are slid under the furnace and function to raise the furnace above the floor's surface. The prior technique does not provide for any vibration dampening between the furnace cabinet and the masonry block holding the furnace above the floor. Therefore, the vibration and noise is transmitted from the cabinet to the floor. Further, the masonry blocks are physically heavy and do not allow for the sliding into place of the furnace while seated on the masonry blocks.

Heretofore, there has been a need for a lightweight furnace mounting block system for elevating the furnace from the floor and minimizing the transmission of vibration and noise. The means for satisfying this need has escaped those skilled in the art. The present invention satisfies this need in a novel and unobvious way.

SUMMARY OF THE INVENTION

Yet another form of the present invention contemplates a combination, comprising: a furnace; and, a plurality of furnace mounts adapted to hold the furnace above a floor, each of the plurality of mounts comprising: a substantially rigid main body member having a first surface adapted to engage the floor and a second surface spaced from the first surface and adapted to support the furnace above the floor; a vibration dampening component positioned on and connected with the second surface, the vibration dampening component having an outer adhesive surface adapted to engage and couple the main body member with the furnace; and wherein the main body member has a locating portion extending from the second surface to abut an outer surface of the furnace and position the second surface relative to the furnace.

One form of the present invention contemplates a mount for supporting a furnace above the floor. The mount comprising: a main body member having a first surface adapted to engage the floor and a second surface spaced from the first surface and adapted to support the furnace above the floor; and, an adherent component connected with the main body member and located proximate the second surface, the adherent component including an adhesive surface adapted to engage and couple the main body member with the furnace.

Another form of the present invention contemplates a mount for supporting a furnace above the floor, comprising: a substantially rigid main body member having a first surface adapted to engage the floor and a second surface spaced from the first surface and adapted to support the furnace above the floor; a vibration dampening component positioned on and connected with the second surface, the vibration dampening component having an outer adhesive surface adapted to engage and couple the main body member with the furnace; and, wherein the main body member has a locating portion extending from the second surface to abut an outer surface of the furnace and position the second surface relative to the furnace.

In yet another form of the present invention there is contemplated a method for supporting a furnace above the floor. The method comprising: providing a furnace mounting block having an adhesive surface and a locating feature; lifting the furnace to place at least a portion of a bottom surface of the furnace off of the floor; positioning the furnace mounting block adjacent the bottom surface of the furnace and abutting the locating feature against an outer surface of the furnace; and adhering the adhesive surface to the bottom surface of the furnace.

One object of the present invention is to provide a unique furnace mounting system.

Related objects and advantages of the present invention will be apparent from the following description.

DESCRIPTION OF THE PREFERRED EMBODIMENTS

Figure 1:
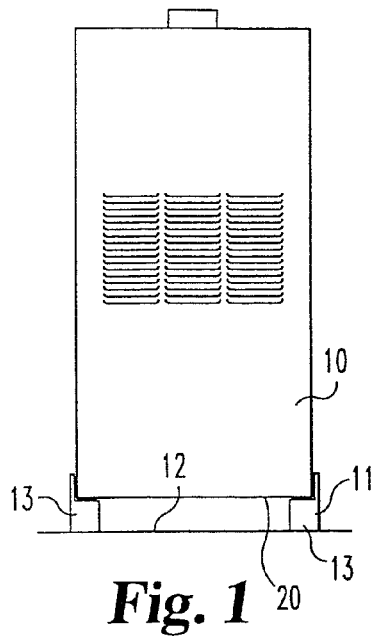
FIG. 1 is an end view of a typical furnace positioned on one embodiment of the furnace mounting blocks of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With reference to FIG. 1, there is illustrated a front view of a typical upflow furnace 10 located on one embodiment of a furnace installation system 11 of the present invention. The furnace installation system 11 is adapted to elevate the furnace 10 from a floor 12. While the present invention will be described with reference to an upflow furnace, it should be understood by one of ordinary skill in the art that the furnace installation system 11 could be utilized with other types of furnaces and air conditioning equipment.

Figure 2:
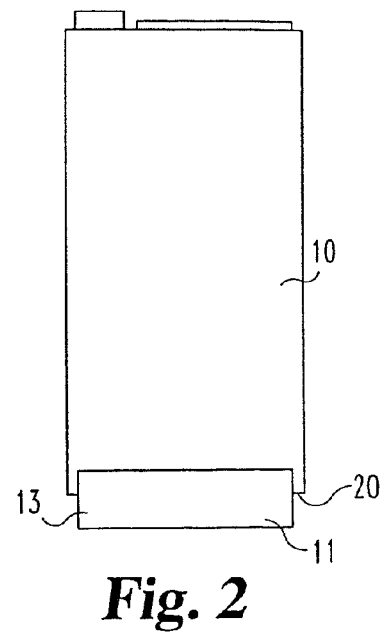
FIG. 2 is a side elevational view of the furnace positioned on the furnace mounting blocks of FIG. 1.
Figure 3:
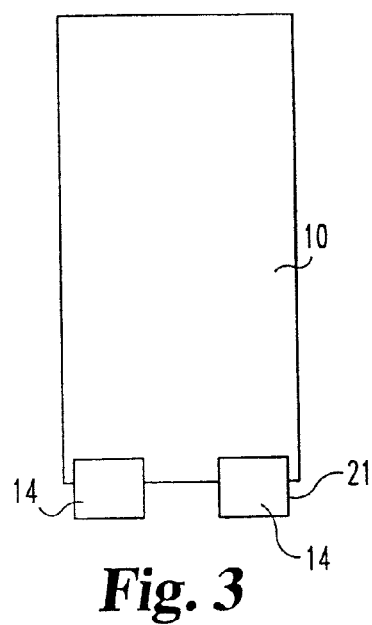
FIG. 3 is a side elevational view of a typical furnace positioned on an alternative embodiment of the furnace mounting blocks of the present invention.

With reference to FIG. 2, there is illustrated a side view of the furnace 10 positioned on the furnace installation system 11. In one embodiment of the present invention the furnace installation system 11 includes a pair of spaced members 13 that are positioned between the bottom surface 20 of the furnace and the floor 12. With reference to FIG. 3, there is illustrated a side view of the furnace 10 positioned on another embodiment of the furnace installation system 21. The furnace installation system 21 includes a member 14 located proximate each of the four corners of the furnace 10. It is contemplated herein that other embodiments of the furnace installation system can contain other quantities of members having different lengths and geometric configurations.

Figure 4:
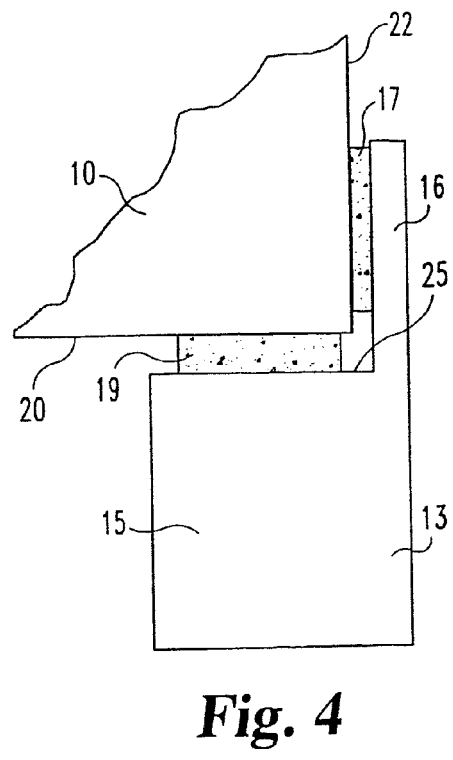
FIG. 4 is an enlarged partial view of FIG. 1, comprising the furnace coupled with the furnace mounting blocks.

With reference to FIG. 4, there is illustrated an enlarged end view of one of the members 13 forming a portion of the furnace installation system 11. The furnace installation system will be described with regards to the installation system 11, however it is understood that it is equally applicable to the other systems contemplated herein. The member 13 includes a floor elevation body member portion 15 and an upstanding attachment member portion 16. The floor elevation body member can be formed as a solid member, a hollow member or other forms provided it has the structural integrity to support the load of the furnace. The member 13 can be formed as a fabricated structure from multiple pieces of material or can be integrally formed as one piece. In one form the member 13 is formed by welding a metal floor elevation body member portion to the upstanding metal member attachment portion. However, in another form the member is integrally formed from a metallic material. The present invention further contemplates that the member can be formed of materials other than metal including, but not limited to, composite materials, polymeric materials, synthetic organic materials and/or plastic. In One form the member is integrally formed of a composite material, a polymeric material, a synthetic material and/or a plastic. The upstanding attachment member portion 16 is secured to the outer surface 22 of the furnace 10. In one form the upstanding attachment member portion 16 is secured to the outer surface 22 by an adhesive material 17. In a preferred form, the upstanding attachment member portion 16 is secured to the outer surface 22 by double-sided tape. The adhesive material 17 can extend along the entire length of the attachment member portion 16 or can extend along only a portion of the attachment member portion 16.

The bottom surface, 20 of the furnace 10 rests on a vibration dampening pad 19 that is coupled to the floor elevation body member 15. The vibration dampening pad 19 extending substantially along the upper surface 25 of the body member 15 and is adapted to dampen vibration and noise associated with the furnace 10. In one form, an elastomeric material defines the pad member 19. The elastomeric materials can include, but are not limited to, polymeric materials and rubber.

The furnace installation system is coupled to the furnace 10 with the adhesive material 17 and the furnace cabinet rests upon the vibration dampening pads 19. The coupling of the members 13 to the furnace 10 allows for the alignment and/or movement of the furnace 10 without necessitating the repositioning of the members 13. Therefore, in one form of the present invention the furnace can be moved around to position the furnace without having to reset the members holding the furnace off the floor. The members 13 functioning to hold the furnace off of the floor, the vibration dampening pads cushion the furnace cabinet to enhance noise reduction, and the system allows the furnace to be positioned without having to reposition the members 13.

Figure 5:
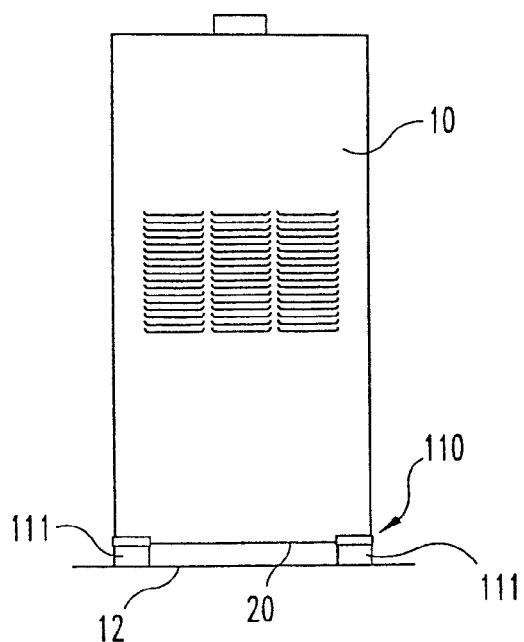
FIG. 5 is an end view of a typical furnace mounted on another embodiment of the furnace mounting blocks of the present invention.
Figure 6:
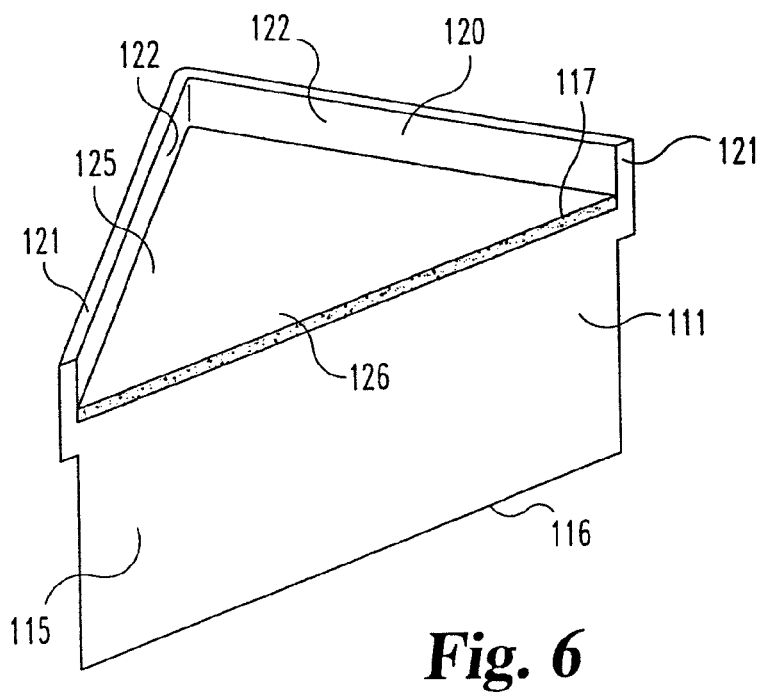
FIG. 6 is a perspective view of the furnace mounting block comprising a portion of FIG. 5.
Figure 7:
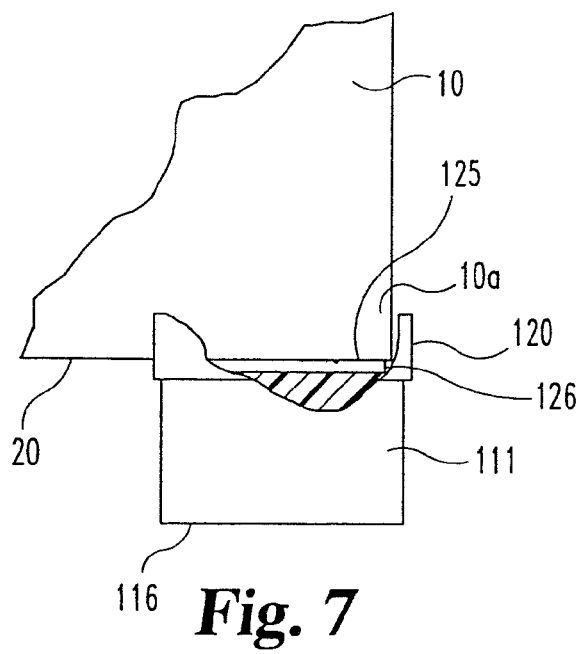
FIG. 7 is an enlarged partially fragmented view of FIG. 5 showing the coupling of the furnace mounting block to the furnace.
Figure 8:
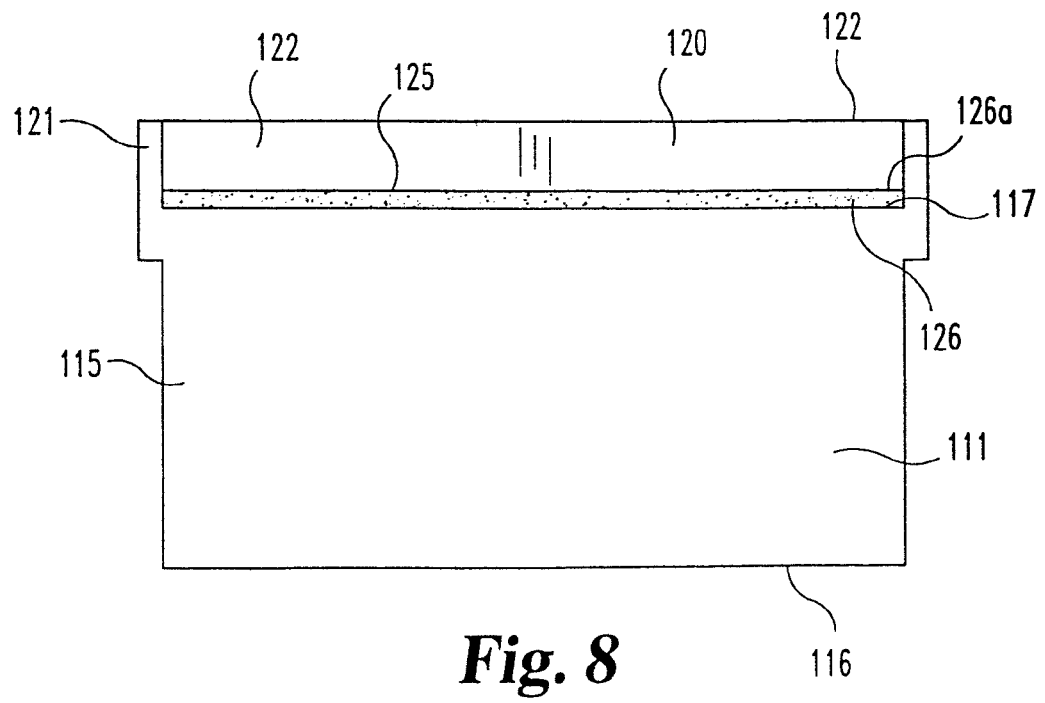
FIG. 8 is a front elevational view of the furnace mounting block of FIG. 6.

With reference to FIG. 5, there is illustrated another embodiment of the furnace installation system 110 of the present invention. As previously described for other forms of the present invention the furnace installation system elevates the bottom surface 20 of the furnace 10 from the floor 12. The furnace installation system 110 preferably includes a plurality of furnace mounting blocks 111 positioned between the floor 12 and the bottom surface 20 of the furnace 10. More preferably, the furnace installation system 110 includes one furnace mounting block 111 located at each of the four corners of the furnace 10. However, the present invention contemplates other furnace installation systems including other quantities of furnace mounting blocks 111 and the location and spacing of them around the bottom surface 20 of the furnace.

With reference to FIGS. 6-11, there is illustrated one form of the furnace mounting block 111. The furnace mounting block 111 includes a main body member 115 and a surface 116 adapted for abutting the floor and another surface 117 adapted for receiving the furnace 10 thereon. In the present application the surface 117 will be considered to receive the furnace thereon if the furnace directly contacts the surface 117 or if the furnace contacts one or a series of intermediate components/materials/layers that are received on and supported by surface 117. In one form of the present invention the first surface 116 and the second surface 117 are spaced apart at least about 2 inches. However it is understood that the present invention is not limited to surfaces spaced apart by the above dimensions and other spacing are contemplated herein. Further, in one form of the present invention the surfaces 116 and 117 are substantially parallel. However, the surfaces 116 and 117 may be other than parallel and they may be contoured and non-planar to meet the specific requirements of some furnace installations.

The furnace mounting block 111 preferably includes at least one locating portion 120 that is adapted to abut the outer surface 10a of the furnace. The positioning of the locating portion 120 adjacent the outer surface 10a of the furnace 10 causes the surface 117 to be properly located and aligned with the bottom surface 20 of the furnace 10. In one form of the present invention an upstanding member 121 that extends from surface 117 defines the locating portion 120. In a preferred form of the present invention the upstanding member 121 extends substantially perpendicular from the surface 117. In a more preferred form of the present invention the locating portion 120 is defined by a pair of upstanding members 121 that are oriented perpendicular to one another and have bearing surfaces 122 adapted to abut the outer surface 10a of the furnace. The locating portion 120 is designed and constructed to mate with the corner configuration of the furnace. Those of ordinary skill in the art should understand that many furnaces do not have a totally enclosed bottom surface, rather they have a lip formed by the sheet metal furnace cabinet. The sheet metal lip generally extents perpendicular from the outer surface 10a back under the furnace about ⅝ inches, however other lip sizes are contemplated herein.

The present invention is applicable with all types of furnaces whether they have a total bottom surface or a lip.

In one form of the present invention the furnace mounting block 111 includes an adherent layer/material 125 coupled with at least a portion of surface 117. The adherent layer/material 125 includes an adhesive material on an outer surface that is adapted to stick to the bottom surface 20 of the furnace 10. The adhesive material securely couples the furnace mounting block 111 with the furnace 10. In one form of the present invention the adhesive material is a double backed tape, however other materials such as, but not limited to, glue are contemplated herein. In a preferred form of the present invention a layer of material that covers the substantial entire surface 117 defines the adherent layer/material 125.

In a more preferred form of the present invention a vibration dampening material 126 is located on and supported by the surface 117. The vibration dampening material 126 may form a part of the adherent layer/material 125 or be positioned between the surface 117 and the adherent layer 125. The vibration dampening material 126 provides for the dampening of vibration and noise that may be transmitted from the furnace to the furnace mounting block 111. The vibration dampening material functions to reduce or eliminate the transmission of noise and/or vibration from the furnace. A layer located on the surface 117 preferably defines the vibration dampening material 126 and in one form has a thickness within the range of about ⅛ to about ¼ inches. However, other thicknesses are contemplated herein. Vibration dampening materials suitable for this application include, but are not limited to, an elastomeric material and/or a cork material. A vibration dampening pad having an elastomeric outer layer and a cork inner portion is also contemplated herein. In a preferred form of the present invention the vibration dampening material is formed of cork. The vibration dampening material is preferably connected to the surface 117 and includes the adherent layer/material 125 on its outer surface 126a. The adhesive material is preferably applied in a fashion that allows it to be substantially parallel with the surface 117. In one form of the present invention a removable layer (not illustrated) covers the adhesive material and prevents contamination of the adhesive prior to installation.

Figure 9:
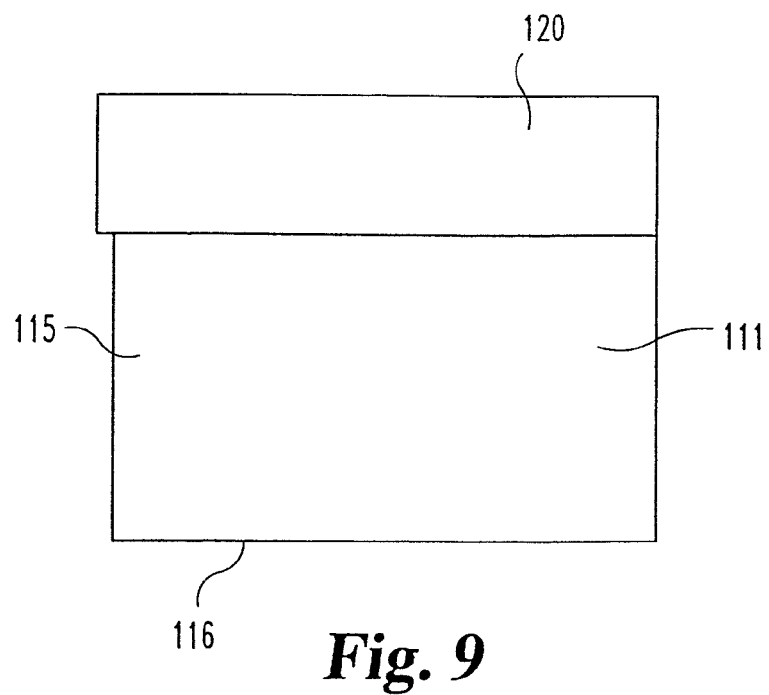
FIG. 9 is a side elevational view of the furnace mounting block of FIG. 6.
Figure 10:
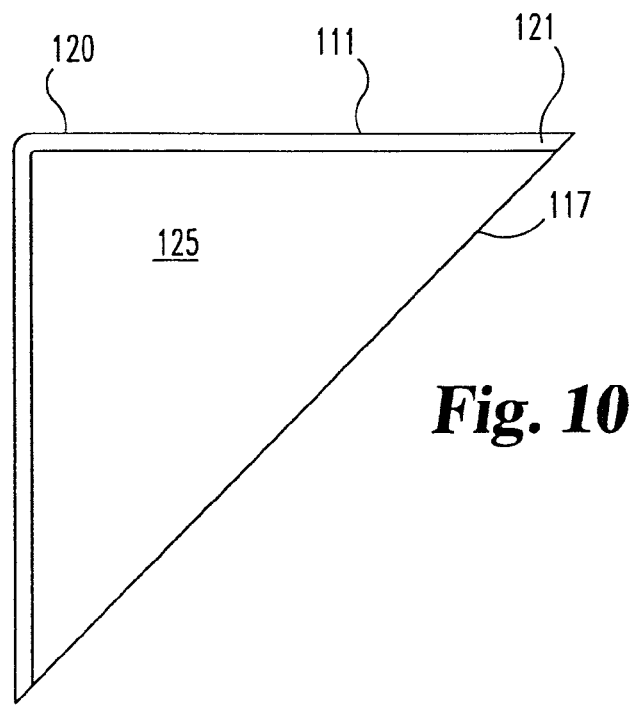
FIG. 10 is a top plan view of the furnace mounting block of FIG. 6.

With reference to FIG. 9, there is illustrated a side view of one form of the furnace mounting block 111. The furnace mounting block 111 in FIG. 9 has the locating portion 120 extending outwardly from the rest of the main body member 115. The present invention contemplates that the locating portion 120 may be configured to have the same width as the main body member 115 and not extend outwardly therefrom. Further, the main body member is contemplated as being formed as an integral component or as a multi-part assembled structure. The main body member is preferably formed as an integral component of materials selected from a group of metals, composite materials, polymeric materials, synthetic materials and/or plastic. Preferably the main body member is formed of a polymeric material, and the material and structure can withstand the static loads associated with supporting a furnace.

The furnace mounting block 111 and furnace installation system has been described with the aid of the figures. A method of installing a furnace on the mounting blocks III will now be set forth. The furnace 10 is raised from the floor 20 so that at least a portion of the bottom surface 20 is clear from the floor 12. If the furnace mounting block III includes a protective cover over the adhesive material it must be removed before installation. The furnace mounting block with the adhesive exposed is positioned proximate the bottom surface 20 of the furnace 10. The locating portion 120 of the furnace mounting block III is brought into an abutting and aligning relationship with the outer surface 10a of the furnace 10. The adhesive surface is brought into contact with the bottom surface 20 of the furnace and adhered to the furnace. The procedure is repeated for each mounting location for the furnace. In a preferred form of the present invention the locating portion 120 is brought into an abutting relationship with each corner adjacent the bottom surface of the furnace. The furnace 10 is then lowered back onto the floor and can be slid into position as desired.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. A mount for supporting a furnace above the floor, comprising:
a substantially non-deformable main body member having a first surface adapted to engage the floor and a second surface spaced an unchangeable fixed distance from and formed parallel to said first surface and adapted to support the furnace above the floor; and an adherent component connected with said main body member and located proximate said second surface; a vibration dampening portion positioned between said adherent component and the furnace; and wherein said body member permits sliding movement of the furnace relative to the floor while supporting the furnace.

2. The mount of claim 1, wherein said main body member includes a locating portion adapted to abut the furnace and align said second surface under the furnace.

3. The mount of claim 2, wherein said locating portion includes an upstanding member extending substantially perpendicular from said second surface.

4. The mount of claim 3, wherein said adherent component is located on said upstanding member, and which further includes a vibration dampening material located on said upstanding member.

5. The mount of claim 4, wherein said vibration dampening material is defined by an elastomeric material.

6. The mount of claim 4, wherein said vibration dampening material is defined by a cork material.

7. The mount of claim 4, wherein said vibration dampening material is defined by an elastomeric and cork configuration.

8. The mount of claim 1, wherein said adherent component is attached to said second surface, and wherein an adhesive surface is spaced from said second surface.

9. The mount of claim 8, wherein said adhesive surface is substantially parallel with said second surface.

10. The mount of claim 1, wherein said vibration dampening portion includes an adhesive surface.

11. The mount of claim 1, wherein said vibration dampening portion includes an elastomeric material.

12. The mount of claim 1, wherein said vibration dampening portion includes a cork material.

13. The mount of claim 1, wherein said vibration dampening portion includes a vibration dampening pad.

14. The mount of claim 1 wherein said second surface is spaced from said first surface at least about 2 inches.

* * * * *